(12) United States Patent
Dairiki et al.

(10) Patent No.: US 10,448,642 B2
(45) Date of Patent: Oct. 22, 2019

(54) COMPOSITION FOR PREPARING EMULSION OR MICROEMULSION

(71) Applicant: Nippon Soda Co., Ltd., Chiyoda-ku, Tokyo (JP)

(72) Inventors: Hiroshi Dairiki, Odawara (JP); Minoru Sakatani, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 247 days.

(21) Appl. No.: 15/128,200

(22) PCT Filed: Mar. 25, 2015

(86) PCT No.: PCT/JP2015/059042
§ 371 (c)(1),
(2) Date: Sep. 22, 2016

(87) PCT Pub. No.: WO2015/147024
PCT Pub. Date: Oct. 1, 2015

(65) Prior Publication Data
US 2017/0112134 A1   Apr. 27, 2017

(30) Foreign Application Priority Data

Mar. 28, 2014 (JP) .................................. 2014-067692

(51) Int. Cl.
| | | |
|---|---|---|
| *A01N 47/40* | (2006.01) | |
| *A01N 25/30* | (2006.01) | |
| *A01N 25/04* | (2006.01) | |
| *B27K 3/34* | (2006.01) | |
| *B27K 3/36* | (2006.01) | |
| *B27K 3/38* | (2006.01) | |
| *B27K 3/50* | (2006.01) | |
| *B27K 3/00* | (2006.01) | |
| *B27K 3/08* | (2006.01) | |
| *B27K 3/15* | (2006.01) | |

(52) U.S. Cl.
CPC ............. *A01N 47/40* (2013.01); *A01N 25/04* (2013.01); *A01N 25/30* (2013.01); *B27K 3/005* (2013.01); *B27K 3/08* (2013.01); *B27K 3/153* (2013.01); *B27K 3/343* (2013.01); *B27K 3/36* (2013.01); *B27K 3/38* (2013.01); *B27K 3/50* (2013.01); *B27K 2240/20* (2013.01)

(58) Field of Classification Search
CPC ........ A01N 47/40; A01N 25/30; A01N 25/04; B27K 3/005; B27K 3/343; B27K 3/36; B27K 3/38; B27K 3/50; B27K 2240/20
See application file for complete search history.

(56) References Cited

U.S. PATENT DOCUMENTS

| | | | |
|---|---|---|---|
| 5,037,653 | A | 8/1991 | Dawson |
| 8,435,928 | B2 * | 5/2013 | Kikugawa ............... A01N 25/30 504/244 |
| 2004/0132621 | A1 | 7/2004 | Frisch et al. |
| 2009/0018022 | A1 | 1/2009 | Yoshii et al. |
| 2010/0234227 | A1 | 9/2010 | Maier et al. |
| 2010/0234232 | A1 | 9/2010 | Dairiki et al. |
| 2011/0124590 | A1 * | 5/2011 | Sowa ..................... A01N 25/04 514/37 |

FOREIGN PATENT DOCUMENTS

| | | |
|---|---|---|
| CA | 2660023 A1 * | 2/2014 |
| CN | 101171916 A | 5/2008 |
| JP | 02-502821 A | 9/1990 |
| JP | 07-041416 A | 2/1995 |
| JP | 09-052810 A | 2/1997 |
| JP | 2006-008601 A | 1/2006 |
| JP | 2006-509807 A | 3/2006 |
| JP | 2006-199687 A | 8/2006 |
| JP | 2007-284437 A | 11/2007 |
| JP | 2007-308440 A | 11/2007 |
| JP | 2010-500299 A | 1/2010 |
| WO | WO 2008/017378 A2 | 2/2008 |
| WO | WO 2009/063608 A1 | 5/2009 |

OTHER PUBLICATIONS

SIGMA-ALDRICH Info (GENAPOL X-080) obtained online via www.sigmaaldrich.com on Jul. 19, 2018. (Year: 2018).*
International Search Report dated Jun. 16, 2015, in PCT/JP2015/059042.
Office Action dated Jul. 26, 2017 in CN 201580015873.2, with machine English translation.
Zhang, Ruiting, "Chapter 5, Emulsion in Water," Liquid Preparations, Guo Wugen Ed., 2004, 90-95, with English translation.

* cited by examiner

*Primary Examiner* — Mina Haghighatian
*Assistant Examiner* — Mei Ping Chui
(74) *Attorney, Agent, or Firm* — Foley & Lardner LLP

(57) ABSTRACT

A composition for preparing an emulsion or microemulsion, the composition including the following components (A) to (D):
  component (A): an active ingredient having a solubility in water at 20° C. of 200 ppm or less;
  component (B): a water-insoluble solvent having no alcohol group;
  component (C): at least one nonionic surfactant selected from the group consisting of a polyoxyalkylene alkyl ether, a polyoxyalkylene alkenyl ether, a polyoxyalkylene alkyl amino ether, and a polyoxyalkylene alkenyl amino ether; and
  component (D): a monohydric alcohol having 8 to 12 carbon atoms.

7 Claims, No Drawings

US 10,448,642 B2

COMPOSITION FOR PREPARING EMULSION OR MICROEMULSION

CROSS-REFERENCE TO RELATED APPLICATIONS

This application is a National Stage application of PCT/JP2015/059042, filed Mar. 25, 2015, which claims priority from Japanese application JP 2014-067692, filed Mar. 28, 2014.

TECHNICAL FIELD

The present invention relates to a composition for preparing an emulsion or microemulsion. More specifically, the present invention relates to a composition for preparing an emulsion or microemulsion with which the solid content does not precipitate even in long term storage, and an emulsion or microemulsion having excellent stability can be obtained by dilution with water.

Priority is claimed on Japanese Patent Application No. 2014-067692, filed Mar. 28, 2014, the content of which is incorporated herein by reference.

BACKGROUND ART

Emulsions and microemulsions have been known as one of the dosage forms of agricultural chemicals, industrial preservatives, or the like. Emulsions (EW (emulsions, oil in water) or CE (concentrated emulsions)) are milky white formulations formed by emulsifying and dispersing an active ingredient insoluble in water as emulsion particles having an average particle size of about greater than 0.1 μm in water by an emulsifier. Microemulsions (ME) are transparent formulations formed by emulsifying and dispersing an active ingredient insoluble in water as fine emulsion particles having an average particle size of about 0.1 μm or less in water by an emulsifier. Emulsions or microemulsions can be obtained by diluting a composition containing an active ingredient insoluble in water, an emulsifier and other components with water, when used as agricultural chemicals or industrial preservatives.

A variety of compositions for obtaining an emulsion or microemulsion by dilution with water have been proposed.

For example, Patent Document 1 discloses a composition for wood preserving, termite repelling and antifungal agents that contains a polyoxyalkylene alkyl ether as an active ingredient.

Patent Document 2 discloses a composition containing an agrochemical active ingredient, a non-alcoholic organic solvent, an anionic surfactant and a nonionic surfactant (polyoxyalkylene alkyl ether or the like).

Patent Document 3 discloses a composition containing a cyclohexanedione-based herbicide, an aromatic hydrocarbon, a polyoxyethylene alkyl ether, and an alkylbenzenesulfonate amine salt.

Patent Document 4 discloses a composition containing an agrochemical active substance, an aromatic hydrocarbon, a polyoxyalkylene aryl phenyl ether, an alcohol such as decanol, and dialkylsulfosuccinate.

Patent Document 5 discloses a composition that contains an agrochemical active ingredient, an aromatic hydrocarbon, a polyoxyalkylene aryl phenyl ether and lauryl alcohol, but does not contain any of anionic surfactants and cationic surfactants.

Patent Document 6 discloses a composition containing a herbicidal active ingredient, a polyoxyethylene-polyoxypropylene block polymer as an emulsifier, a polyoxyethylene alkylamino ether and/or a higher alcohol as an emulsion stabilizer, an aromatic organic solvent and water.

CITATION LIST

Patent Documents

[Patent Document 1] Japanese Unexamined Patent Application, First Publication No. 2006-199687
[Patent Document 2] Published Japanese Translation No. 2006-509807 of the PCT International Publication
[Patent Document 3] Japanese Unexamined Patent Application, First Publication No. 2006-8601
[Patent Document 4] PCT International Publication No. WO 2008/017378A
[Patent Document 5] PCT International Publication No. WO 2009/063608A
[Patent Document 6] Japanese Unexamined Patent Application, First Publication No. Hei 09-52810

SUMMARY OF INVENTION

Technical Problem

With respect to the compositions according to these prior art documents, stability of the resulting emulsion or microemulsion is not sufficient and solid content is sometimes precipitated, and thus there is a difficulty in long term storage or long term efficacy maintenance.

An object of the present invention is to provide a composition for preparing an emulsion or microemulsion with which the solid content does not precipitate even in long term storage, and an emulsion or microemulsion having excellent stability can be obtained by dilution with water.

Solution to Problem

As a result of intensive studies in order to solve the above problems, the inventors of the present invention have completed the present invention including the following embodiments.

[1] A composition for preparing an emulsion or microemulsion, the composition including the following components (A) to (D):
component (A): an active ingredient having a solubility in water at 20° C. of 200 ppm or less;
component (B): a water-insoluble solvent having no alcohol group;
component (C): at least one nonionic surfactant selected from the group consisting of a polyoxyalkylene alkyl ether, a polyoxyalkylene alkenyl ether, a polyoxyalkylene alkyl amino ether, and a polyoxyalkylene alkenyl amino ether; and
component (D): a monohydric alcohol having 8 to 12 carbon atoms.

[2] The composition for preparing an emulsion or microemulsion according to the above [1], further including a component (E): water.

[3] The composition for preparing an emulsion or microemulsion according to the above [2],
wherein relative to the mass of the composition, the component (A) is from 1 to 30% by mass, the component (B) is from 5 to 40% by mass, the component (C) is from 10 to 80% by mass, the component (D) is from 1 to 20% by mass, and the component (E) is equal to or less than 60% by mass;

relative to the mass of the component (B), the component (A) is equal to or less than 100% by mass; and a component (G): a nonionic surfactant other than the component (C) may be contained, and the total amount of the component (C) and the component (G) is from 100 to 1,000% by mass, relative to the mass of the component (B).

[4] The composition for preparing an emulsion or microemulsion according to the above [3], wherein the total amount of the component (C) and the component (G), relative to the mass of the composition, is from 20 to 80% by mass.

[5] The composition for preparing an emulsion or microemulsion according to any one of the above [1] to [4], wherein the component (A) is at least one active ingredient selected from the group consisting of an insecticide, a bactericide, a fungicide, a preservative, an algicide and a herbicide.

[6] The composition for preparing an emulsion or microemulsion according to any one of the above [1] to [5], wherein the component (B) is an aromatic hydrocarbon.

[7] The composition for preparing an emulsion or microemulsion according to any one of the above [1] to [6], wherein the component (D) is lauryl alcohol.

[8] The composition for preparing an emulsion or microemulsion according to any one of the above [1] to [7], further including a component (F): an active ingredient other than the component (A).

[9] The composition for preparing an emulsion or microemulsion according to the above [8], wherein the component (F) is a neonicotinoid-based insecticide.

[10] A wood preservative including the composition for preparing an emulsion or microemulsion according to any one of the above [1] to [9].

Advantageous Effects of Invention

With respect to the composition for preparing an emulsion or microemulsion according to the present invention, the solid content does not precipitate in long term storage, and the emulsion or microemulsion having excellent stability can be obtained by dilution with water.

DESCRIPTION OF EMBODIMENTS

The composition for preparing an emulsion or microemulsion according to the present invention includes a component (A), a component (B), a component (C), and a component (D), and, if necessary, a component (E) and/or a component (F).

(Emulsion or Microemulsion)

An emulsion is a state in which a solution obtained by diluting in water resulted in the generation of milky white emulsified particles, and a microemulsion is a state in which a solution obtained by diluting in water becomes transparent and generates numerous soluble materials that are finer than the emulsified particles. The phrase "emulsion or microemulsion" used in the present invention indicates that an emulsion may be generated or a microemulsion may be generated when diluted in water, and also indicates that the liquid obtained by diluting in water may have a milky white color or may be transparent. Further, the term "composition for preparing an emulsion or microemulsion" indicates that an emulsion or a microemulsion is generated when diluted in water, and also indicates that it may have a milky white color or it may be transparent.

(Component (A))

The component (A) may be a liquid or a solid, which is an active ingredient with a solubility in water at 20° C. of 200 ppm or less. The component (A) is difficult to become homogeneous in water as long as it is not made into a form of emulsion or microemulsion because of the very low solubility in water. In addition, even if it is possible to form the component (A) into an emulsion or a microemulsion, aggregates are generated immediately and the growth of the crystal is likely to occur. The component (A) is preferably at least one active ingredient selected from the group consisting of an insecticide, a bactericide, a fungicide, a preservative, an algicide and a herbicide.

Specific examples of the component (A) include the followings.

Insecticides: phosalone, carbaryl, tralomethrin, deltamethrin, bifenthrin, deltamethrin, etofenprox, cyfluthrin, acrinathrin, cypermethrin, fenpropathrin, tefluthrin, fenvalerate, fipronil, novaluron, bistrifluron, buprofezin, chlorfluazuron, diflubenzuron, teflubenzuron, hexaflumuron, lufenuron, triflumuron, flufenoxuron, chromafenozide, tebufenozide, fenpyroximate, methoxyfenozide and hydramethylnon;

Bactericides/Fungicides/Preservatives: hexaconazole, tebuconazole, cyproconazole, propiconazole, metconazole, epoxiconazole, myclobutanil, triflumizole, imazalil, triforine, tludioxonil, azoxystrobin, pyraclostrobin, trifioxystrobin, kresoxim-methyl, thiocyanatomethylthio benzothiazole (benthiazole, TCMTB), 2-(4-thiazolyl) benzimidazole (thiabendazole), methyl benzimidazol-2-yl carbamate (carbendazim, BCM), methyl 1-butylcarbamoyl benzimidazol-2-yl carbamate (benomyl), thiophanate methyl, cyprodinil, 2,4,5,6-tetrachloroisophthalonitrile (chlorothalonil), iminoctadine albesilate, iprodione, procymidone, diethofencarb, fluor folpet, dichlofluanid, cyflufenamid, boscalid, 3-iodo-2-propynyl butyl carbamate (IPBC), diiodomethyl-p-tolylsulfone (DIMPTS), 2-butyl-1,2-benzisothiazolin-3-one (BBIT), 4,5-dichloro-2-octyl-4-isothiazolin-3-one (DCOIT), 2,3,5,6-tetrachloro-4-sulfonylmethylpyridine (TCMSP) and biphenyl;

Algicides/Herbicides: diuron (DCMU), daimuron, metobenzuron, cumyluron, nicosulfuron, cybutryne, terbutryn, simazine, atrazine, propazine, cyanazine, dimethametryn, prometryn, butralin, benfluralin, prodiamine, benzofenap, pyraflufen-ethyl, bifenox, bromobutide, bromoxynil, propanil, diflufenican, mefenacet, clomeprop, diclosulam, dithiopyr, isoxaben, lenacil, pyributicarb, pyriminobac-methyl, oxadiazon, oryzalin, oxadiargyl, fluthiacet-methyl, pyribenzoxim and pentoxazone.

Of these, the component (A) is preferably bifenthrin, etofenprox, fipronil, novaluron, hexaconazole, cyproconazole, propiconazole, tebuconazole, thiabendazole, fludioxonil, IPBC, BBIT, DCOIT, TCMTB, TCMSP, DCMU and cybutryne, and IPBC and hexaconazole are particularly preferred.

The component (A) is preferably one which is soluble in the component (B). Therefore, from the viewpoint of solubility in the component (B), it is preferable to ensure that the component (A) is 100% by mass or less, relative to the mass of the component (B).

The content of the component (A) is preferably from 1 to 30% by mass, and more preferably from 5 to 15% by mass, relative to the mass of the composition. The mass of the composition indicates a total amount of the composition obtained by adding all the components (A) to (G) and other components. Hereinafter, the phrase "mass of the composition" has the same meaning as defined above.

(Component (B))

The component (B) is a water-insoluble solvent having no alcohol group. The component (B) is preferably one that is in the form of a liquid at 20° C. and has a solubility in water at 20° C. of 1,000 ppm or less.

Examples of the component (B) include aliphatic hydrocarbons such as hexane, cyclohexane, heptane, isooctane, decane, decalin and liquid paraffin; aromatic hydrocarbons such as benzene, toluene, xylene, ethylbenzene, cumene, methylnaphthalene, dimethylmonoisopropylnaphthalene, dimethyldiisopropylnaphthalene, phenylxylylethane, and petroleum aromatic hydrocarbons; carboxylic acid esters such as vegetable oils and higher fatty acid esters; and mixtures of the water-insoluble solvents described above. Among these, as the component (B), aromatic hydrocarbons are preferred. Preferable examples of the aromatic hydrocarbon used as the component (B) include Solvesso 100, Solvesso 150 and Solvesso 200 (Solvesso is a registered trademark of Exxon Mobil Corporation), and Nisseki Hisol SAS 296 (Nisseki Hisol is a registered trademark of JX Nippon Oil & Energy Corporation). Of these, Nisseki Hisol SAS 296 is preferred.

The content of the component (B) is preferably from 5 to 40% by mass, and more preferably from 10 to 20% by mass, relative to the mass of the composition.

(Component (C))

The component (C) has an ether structure in which a polyoxyalkylene chain and one group selected from the group consisting of an alkyl group, an alkenyl group, an alkylamino group and an alkenylamino group are bonded by an oxygen atom. More specifically, the component (C) is at least one nonionic surfactant selected from the group consisting of a polyoxyalkylene alkyl ether, a polyoxyalkylene alkenyl ether, a polyoxyalkylene alkyl amino ether, and a polyoxyalkylene alkenyl amino ether. Among these, as the component (C), a polyoxyalkylene alkyl ether and a polyoxyalkylene alkyl amino ether are preferred.

The degree of polymerization of the polyoxyalkylene chain in the component (C) is preferably from 4 to 50, and more preferably from 4 to 25.

Examples of the polyoxyalkylene chain include a polyoxyethylene chain, a polyoxypropylene chain, a polyoxybutylene chain, and a copolymer chain composed of polyoxyethylene and polyoxypropylene. Of these, a polyoxyethylene chain is preferred.

The alkyl group, alkenyl group, alkylamino group or alkenylamino group in the component (C) preferably has 6 to 30 carbon atoms, and more preferably has 10 to 18 carbon atoms.

Further, the component (C) is a useful component for stably making the components (A) and (B) homogeneous in water, together with the component (D). Accordingly, the component (C) is a compound which is selected from among nonionic surfactants, as a surfactant to stably making the components (A) and (B) homogeneous in water, together with the component (D).

The content of the component (C) is preferably from 10 to 80% by mass, and more preferably from 15 to 70% by mass, relative to the mass of the composition.

(Component (G): Nonionic Surfactant Other than the Component (C))

The component (G) is a nonionic surfactant other than the component (C), and the composition for preparing an emulsion or microemulsion according to the present invention may contain the component (G). Further, the component (G) is not a component contributing alone to the stabilization, but contributes to the stabilization together with the component (C). Examples of the component (G) include polyoxyalkylene vegetable oil ethers such as polyoxyethylene castor oil ethers.

The content of the component (G) is an amount within the range that does not adversely affect the effects of the present invention. More specifically, the total amount of the component (C) and the component (G) is preferably from 100 to 1,000% by mass, more preferably from 100 to 800% by mass, and still more preferably from 200 to 800% by mass, relative to the mass of the component (B).

Further, the total content of the component (C) and the component (G) is preferably from 20 to 80% by mass, and more preferably from 40 to 70% by mass, relative to the mass of the composition.

(Component (D))

The component (D) is a monohydric alcohol having 8 to 12 carbon atoms. The component (D) may be either a linear alcohol or a branched alcohol. Examples of the component (D) include capril alcohol (also known as: n-octanol), iso-octanol, s-octanol, n-nonanol, n-decanol, isodecanol, s-decanol, n-undecanol, iso-undecanol, s-undecanol, lauryl alcohol (also known as: n-dodecanol), s-dodecanol, and the like. Of these, lauryl alcohol is preferred.

The content of the component (D) is preferably from 1 to 20% by mass, and more preferably from 5 to 15% by mass, relative to the mass of the composition.

(Component (E))

The component (E) is water. The water may be soft water or hard water. The content of the component (E) is preferably not more than 60% by mass, and more preferably from 10 to 30% by mass, relative to the mass of the composition. By containing water, it is possible to enhance the safety against fire of the composition for preparing an emulsion or microemulsion. More specifically, as an example of enhancing the safety against fire, since the composition in which the component (E) has been added can further lower the flash point than the composition in which the component (E) has not been added, the component (E) is capable of making the composition more difficult to ignite.

(Component (F))

The component (F) is an active ingredient other than the component (A) and may be a liquid or may be a solid, which is an active ingredient with a solubility in water at 20° C. higher than 200 ppm. The component (F) can be, for example, at least one active ingredient selected from the group consisting of an insecticide, a bactericide, a fungicide, a preservative, an algicide and a herbicide. As the component (F), a neonicotinoid-based insecticide is preferred. Examples of the neonicotinoid-based insecticide include nitenpyram, imidacloprid, acetamiprid, thiamethoxam, clothianidin, thiacloprid, dinotefuran, and the like. Among these neonicotinoid-based insecticides, as the component (F), acetamiprid having a high insecticidal effect against termites or the like is particularly preferable.

In addition, although the component (F) as a preservative is not particularly limited, Bestcide-750 (manufactured by Nippon Soda Co., Ltd.) can be used.

The content of the component (F) is from 0 to 10% by mass, preferably from 0.01 to 10% by mass, and more preferably from 0.1 to 5% by mass, relative to the mass of the composition.

(Other Components)

The composition for preparing an emulsion or microemulsion according to the present invention may contain, in addition to the components (A) to (F), an anionic surfactant, a cationic surfactant, an amphoteric surfactant, a water-soluble organic solvent, an antifoaming agent, an antioxidant, and the like as other components.

The content of the other components is from 0 to 30% by mass, preferably from 0.1 to 30% by mass, and more preferably from 1 to 20% by mass, relative to the mass of the composition.

Although the anionic surfactant is not particularly limited, examples of the anionic surfactant include dialkyl sulfocarboxylic acid esters, alkyl aryl sulfonic acid salts, alkyl sulfonic acid salts, sulfosuccinic acid esters, higher fatty acid alkali salts, polycarboxylic acid salts, polyoxyethylene alkyl ether phosphoric acid ester salts, alkylnaphthalene sulfonic acid salts, formalin condensates of alkylnaphthalene sulfonic acid salts, lignin sulfonic acid salts and the like. For the salts, alkali metals such as lithium, sodium and potassium; alkaline earth metals such as calcium and magnesium; and ammonium and amines such as alkylamines, cycloalkylamines and alkanolamines can be used.

The content of the anionic surfactant is from 0 to 5% by mass, preferably from 0.2 to 3% by mass, and more preferably from 0.5 to 2% by mass, relative to the mass of the composition.

As the cationic surfactant, tetramethylammonium chloride, tetramethylammonium hydroxide, tetrabutylammonium chloride, alkyldimethylbenzylammonium chloride, alkyltrimethylammonium chloride, alkyltrimethylammonium bromide, benzyltrimethylammonium chloride, benzyltriethylammonium chloride, benzalkonium chloride ($C_6H_5CH_2N^+(CH_3)_2RCl^-$) ($R=C_8$ to $C_{18}$), benzalkonium bromide ($C_6H_5CH_2N^+(CH_3)_2RBr^-$) ($R=C_8$ to $C_{18}$), benzethonium chloride ($C_6H_5CH_2N^+(CH_3)_2(CH_2CH_2O)_2C_6H_4C_8H_{17}Cl^-$), dialkyl dimethyl ammonium chloride, monomethylamine hydrochloride, dimethylamine hydrochloride, trimethylamine hydrochloride, alkylpyridinium chloride (in which the alkyl group has 4 to 18 carbon atoms), or the like can be used.

The content of the cationic surfactant is from 0 to 10% by mass, preferably from 0.5 to 5% by mass, and more preferably from 1 to 3% by mass, relative to the mass of the composition.

As the amphoteric surfactant, alkyl dimethyl amino acetic acid betaine ($RN^+(CH_3)_2CH_2COO^-$), alkyl amino methyl dimethyl sulfopropyl betaine ($RN^+(CH_3)_2(CH_2)_3SO_3^-$), alkyl carboxymethyl hydroxyethyl imidazoliniurn betaine ($RC_3H_4N_2(C_2H_4OH)CH_2COO^-$), alkyldimethylamine N-oxide (in which the alkyl group has 4 to 18 carbon atoms), or the like can be used.

The content of the amphoteric surfactant is from 0 to 10% by mass, preferably from 0.5 to 5% by mass, and more preferably from 1 to 3% by mass, relative to the mass of the composition.

The water-soluble organic solvent is not particularly limited, although it preferably has the effect of serving as an antifreezing agent and the effect of dissolving the component (A). Examples of the water-soluble organic solvent preferably used in the present invention include polyols such as ethylene glycol, propylene glycol, acetylene glycol, and glycerin; and glycol ethers such as diethylene glycol, triethylene glycol monobutyl ether, triethylene glycol monomethyl ether, tripropylene glycol monomethyl ether, diethylene glycol monobutyl ether, diethylene glycol monoethyl ether, diethylene glycol monomethyl ether, and the like. Of these, diethylene glycol monomethyl ether is preferred.

The content of the water-soluble organic solvent is from 0 to 30% by mass, preferably from 0.1 to 30% by mass, and more preferably from 1 to 20% by mass, relative to the mass of the composition.

Although the antifoaming agent is not particularly limited, a silicone-based antifoaming agent (KS-538: manufactured by Shin-Etsu Chemical Co., Ltd.), an acetylene glycol-based antifoaming agent, or the like can be used.

As the acetylene glycol-based antifoaming agent, Surfynol 104E is preferred.

The content of the antifoaming agent is from 0 to 1% by mass, preferably from 0.01 to 0.7% by mass, and more preferably from 0.1 to 0.6% by mass, relative to the mass of the composition.

Although the antioxidant is not particularly limited, L-ascorbic acid, isoascorbic acid, dibutylhydroxytoluene, tocopherol, butylhydroxyanisole, or the like can be used.

The content of the antioxidant is from 0 to 10% by mass, preferably from 0.5 to 5% by mass, and more preferably from 1 to 3% by mass, relative to the mass of the composition.

It is possible to obtain an emulsion or a microemulsion by diluting the composition for preparing an emulsion or microemulsion with water for preparation. The water used in the preparation of emulsion or microemulsion may be hard water or may be soft water.

In the present invention, an emulsion or microemulsion is formed by containing the composition for preparing an emulsion or microemulsion and the water for preparation. The total amount of water contained in the composition for preparing an emulsion or microemulsion and the water for preparation is preferably more than 60% by mass, and more preferably equal to or more than 80% by mass, relative to the mass of the emulsion or microemulsion. In addition, the dilution ratio by the water for preparation is, by volume ratio, preferably from 5- to 1,000-fold, and more preferably from 10- to 200-fold.

(Wood Preservative and the Like)

The composition for preparing an emulsion or microemulsion according to the present invention can be used as an agricultural chemical, an industrial preservative, an industrial antiseptic, a wood preservative, or the like. Among these, use as a wood preservative is preferred.

The wood preservative of the present invention is used to treat wood. The above treatment is carried out by coating or spraying the wood preservative of the present invention to the wood surface (surface treatment), pressure injection or impregnation of the wood preservative of the present invention into wood, or the like. The wood preservative of the present invention is particularly suitable for the surface treatment. In the coating or spraying treatment, a brush, a spray or a means such as dipping can be employed.

Since the emulsion or microemulsion obtained using the composition for preparing an emulsion or microemulsion according to the present invention exhibits excellent stability without precipitation of the solid content over a long period of time, even if the emulsion or microemulsion prepared in large quantities is used continuously over a long period of time, the efficacy of wood protection does not decrease. Therefore, there is no need to frequently prepare a new emulsion or microemulsion.

EXAMPLES

Hereinafter, the present invention will be described in more detail with reference to Examples. However, these Examples in no way limit the scope of the present invention. Additions, omissions, substitutions, and other modifications can be made without departing from the spirit or scope of the present invention. The term "parts" in the present Examples refers to parts by mass.

An "aromatic hydrocarbon-based solvent" is a reaction product of styrene and a xylene/ethylbenzene mixture (CAS: 1029912-90-0), and includes, as main components, 1-phenyl-1-xylyl ethane and phenyl ethyl phenyl ethane. The reaction product is manufactured by JX Nippon Oil & Energy Corporation under the trade name of Nisseki Hisol SAS296. Hereinafter, the term "aromatic hydrocarbon-based solvent" indicates this product.

A "silicone-based antifoaming agent" is an antifoaming agent manufactured by Shin-Etsu Chemical Co., Ltd. under the trade name of KS-358. Hereinafter, the term "silicone-based antifoaming agent" indicates this product.

An "acetylene glycol-based antifoaming agent" is an acetylene-based dialcohol composition, and is a mixture of 2,4,7,9-tetramethyl-5-decyne-4,7-diol and ethane-1,2-diol. This composition is manufactured by Air Products Japan, Inc. under the trade name of Surfynol (registered trademark) 104E. Hereinafter, the term "silicone-based antifoaming agent" indicates this product.

Example 1

4.825 parts of diethylene glycol monobutyl ether, 15 parts of the aromatic hydrocarbon-based solvent, 0.015 parts of the silicone-based antifoaming agent, 0.5 parts of the acetylene glycol-based antifoaming agent, 15 parts of water, 10 parts of lauryl alcohol, 20 parts of POE (6) lauryl ether (NEWKALGEN D-1106; manufactured by Takemoto Oil & Fat Co., Ltd.), 25 parts of POE (25) castor oil ether (NEWKALGEN D-225; manufactured by Takemoto Oil & Fat Co., Ltd.) and 0.05 parts of a preservative (Bestcide-750: an aqueous solution of isothiazoline-based compound with a concentration of about 4% by mass, manufactured by Nippon Soda Co., Ltd.) were homogeneously mixed. 1.02 parts of acetamiprid (manufactured by Nippon Soda Co., Ltd.), 2.06 parts of IPBC (manufactured by Arch Chemicals, Inc.) and 6.53 parts of hexaconazole (manufactured by Rallis India Limited) were dissolved in the above mixture solution with stirring to obtain a composition (1) for preparing a microemulsion.

99 ml of tap water was charged into a 110 ml screw tube, and 1 ml of the composition (1) for preparing a microemulsion was added thereto. The screw tube was closed with a lid, turned upside down, and shaken vigorously 10 times to obtain a microemulsion (100-fold diluted solution).

9.5 ml of tap water was charged into a 13.5 ml screw tube, and 0.5 ml of the composition (1) for preparing a microemulsion was added thereto. The screw tube was closed with a lid, turned upside down, and shaken vigorously 10 times to obtain a microemulsion (20-fold diluted solution).

Each screw tube was allowed to stand upright for 150 days at 5° C. The state of the diluted solution in the screw tube was visually observed every day. The number of days until the solid content was precipitated was recorded. The precipitation of solid content was not observed during the 150 days in the aforementioned 100-fold diluted solution and 20-fold diluted solution. The results are shown in Table 1.

Example 2

A composition (2) for preparing a microemulsion was obtained in the same manner as in Example 1 with the exception that the POE (6) lauryl ether was changed to POE (10) lauryl ether (NEWKALGEN D-1110, manufactured by Takemoto Oil & Fat Co., Ltd.).

With respect to the above composition (2), the number of days until the solid content was precipitated was recorded in the same manner as in Example 1. The results are shown in Table 1.

Example 3

A composition (3) for preparing a microemulsion was obtained in the same manner as in Example 1 with the exceptions that the POE (6) lauryl ether was changed to POE (8) oleyl ether (NEWKALGEN D-1508, manufactured by Takemoto Oil & Fat Co., Ltd.), the amount of the POE (25) castor oil ether was changed to 40 parts, and the amount of water was changed to 0 parts.

With respect to the above composition (3), the number of days until the solid content was precipitated was recorded in the same manner as in Example 1. The results are shown in Table 1.

Examples 4 to 7

Compositions (4) to (7) for preparing a microemulsion were obtained in the same manner as in Example 1 with the exception that the compounding prescription was changed to those shown in Table 1.

With respect to the above compositions (4) to (7), the number of days until the solid content was precipitated was recorded in the same manner as in Example 1. The results are shown in Table 1.

Example 8

A composition (8) for preparing a microemulsion was obtained in the same manner as in Example 3 with the exceptions that 20 parts of the POE (8) oleyl ether was changed to 40 parts of POE (15) alkyl amino ether (NEWKALGEN D-3615T, manufactured by Takemoto Oil & Fat Co., Ltd.), the amount of the POE (25) castor oil ether was changed to 15 parts, and the amount of diethylene glycol monobutyl ether was changed to 9.825 parts.

With respect to the above composition (8), the number of days until the solid content was precipitated was recorded in the same manner as in Example 1. The results are shown in Table 1.

Comparative Examples 1 to 4

Compositions (9) to (12) for preparing a microemulsion were obtained in the same manner as in Example 1 with the exception that the compounding prescription was changed to those shown in Table 1.

With respect to the above compositions (9) to (12), the number of days until the solid content was precipitated was recorded in the same manner as in Example 1. The results are shown in Table 1.

TABLE 1

(Unit of composition: parts by mass, Unit of number of days until solid content precipitation: days)

| Composition | Example 1 (1) | Example 2 (2) | Example 3 (3) | Example 4 (4) | Example 5 (5) | Example 6 (6) | Example 7 (7) | Example 8 (8) | Comparative Example 1 (9) | Comparative Example 2 (10) | Comparative Example 3 (11) | Comparative Example 4 (12) |
|---|---|---|---|---|---|---|---|---|---|---|---|---|
| Component (A) | | | | | | | | | | | | |
| Hexaconazole | 6.53 | 6.53 | 6.53 | 6.53 | 6.53 | 6.53 | 6.53 | 6.53 | 6.53 | 6.53 | 6.53 | 6.53 |
| IPBC | 2.06 | 2.06 | 2.06 | 2.06 | 2.06 | 2.06 | 2.06 | 2.06 | 2.06 | 2.06 | 2.06 | 2.06 |
| Component (B) | | | | | | | | | | | | |
| Aromatic hydrocarbon-based solvent | 15 | 15 | 15 | 15 | 15 | 15 | 15 | 15 | 15 | 15 | | |
| Component (C) | | | | | | | | | | | | |
| POE (6) lauryl ether | 20 | | | 20 | | 60 | | | | | | |
| POE (10) lauryl ether | | 20 | | | | | | | | | | 20 |
| POE (8) oleyl ether | | | 20 | | 60 | | 45 | | | | | |
| POE (15) alkyl amino ether | | | | | | | | 40 | | | | |
| Component (G) | | | | | | | | | | | | |
| POE (25) castor oil ether | 25 | 25 | 40 | 40 | | | | 15 | 55 | 65 | 45 | 25 |
| Component (D) | | | | | | | | | | | | |
| Lauryl alcohol | 10 | 10 | 10 | 10 | 10 | 10 | 10 | 10 | 10 | | 10 | 10 |
| Component (E) | | | | | | | | | | | | |
| Water | 15 | 15 | | | | | | | | | 15 | 15 |
| Component (F) | | | | | | | | | | | | |
| Acetamiprid | 1.02 | 1.02 | 1.02 | 1.02 | 1.02 | 1.02 | 1.02 | 1.02 | 1.02 | 1.02 | 1.02 | 1.02 |
| Bestcide-750 | 0.05 | 0.05 | 0.05 | 0.05 | 0.05 | 0.05 | 0.05 | 0.05 | 0.05 | 0.05 | 0.05 | 0.05 |
| Other components | | | | | | | | | | | | |
| Diethylene glycol monobutyl ether | 4.825 | 4.825 | 4.825 | 4.825 | 4.825 | 4.825 | 19.825 | 9.825 | 9.825 | 9.825 | 19.825 | 19.825 |
| Silicone-based antifoaming agent | 0.015 | 0.015 | 0.015 | 0.015 | 0.015 | 0.015 | 0.015 | 0.015 | 0.015 | 0.015 | 0.015 | 0.015 |
| Acetylene glycol-based antifoaming agent | 0.5 | 0.5 | 0.5 | 0.5 | 0.5 | 0.5 | 0.5 | 0.5 | 0.5 | 0.5 | 0.5 | 0.5 |
| Number of days until solid content precipitation | | | | | | | | | | | | |
| 100-fold diluted solution | >150 | >150 | >150 | >150 | >150 | >150 | >150 | >150 | 8 | 30 | 9 | 4 |
| 20-fold dilated solution | >150 | >150 | >150 | >150 | >150 | >150 | >150 | >150 | 30 | 8 | 2 | 4 |

As shown in the above results, the compositions for preparing a microemulsion according to the present invention exhibited very high stability without precipitation of the solid content even when being left standing for 150 days at a low temperature after dilution.

INDUSTRIAL APPLICABILITY

It is possible to provide a composition for preparing an emulsion or microemulsion with which the solid content does not precipitate in long term storage, and an emulsion or microemulsion having excellent stability can be obtained by dilution with water.

The invention claimed is:

1. A composition for preparing an emulsion or microemulsion, the composition comprising the following components (A) to (D):
   component (A): at least one selected from the group consisting of bifenthrin, etofenprox, fipronil, novaluron, hexaconazole, cyproconazole, propiconazole, tebuconazole, thiabendazole, fludioxonil, 3-iodo-2-propynyl butyl carbamate, 2-butyl-1,2-benzisothiazolin-3-one, 4,5-dichloro-2-octyl-4-isothiazolin-3-one, thiocyanatomethylthio benzothiazole, 2,3,5,6-tetrachloro-4-sulfonylmethylpyridine, diuron and cybutryne;
   component (B): a water-insoluble solvent having no alcohol group which is a reaction product of a styrene and a mixture of xylene and ethylbenzene, wherein the reaction product comprises 1-phenyl-1-xylyl ethane and phenyl ethyl phenyl ethane;
   component (C): at least one nonionic surfactant selected from the group consisting of a polyoxyalkylene alkyl ether, a polyoxyalkylene alkenyl ether, a polyoxyalkylene alkyl amino ether, and a polyoxyalkylene alkenyl amino ether; and
   component (D): a monohydric alcohol having 8 to 12 carbon atoms,
   wherein the composition does not contain an anionic surfactant.

2. The composition for preparing an emulsion or microemulsion according to claim 1, further comprising a component (E) which is water.

3. The composition for preparing an emulsion or microemulsion according to claim 2, further comprising a component (F): a neonicotinoid-based insecticide,
   wherein, an amount of the component (A), relative to the mass of the composition, is from 5 to 15% by mass, provided that the amount of the component (A), relative to the mass of the component (B), is equal to or less than 100% by mass,
   an amount of the component (B), relative to the mass of the composition, is from 10 to 20% by mass, an amount of the component (C), relative to the mass of the composition, is from 20 to 60% by mass, an amount of the component (D), relative to the mass of the composition, is from 5 to 15% by mass, an amount of the component (E), relative to the mass of the composition, is 10 to 30% by mass, and an amount of the component (F), relative to the mass of the composition, is 0.1 to 5% by mass.

4. The composition for preparing an emulsion or microemulsion according to claim 3, further comprising a component (G) which is a nonionic surfactant other than the component (C), and wherein a total amount of the component (C) and the component (G), relative to the mass of the composition, is from 40 to 70% by mass.

5. The composition for preparing an emulsion or microemulsion according to claim 1, wherein the component (D) is lauryl alcohol.

6. The composition for preparing an emulsion or microemulsion according to claim 3, wherein the component (F) is acetamiprid.

7. A wood preservative comprising the composition for preparing an emulsion or microemulsion according to claim 1.

* * * * *